United States Patent
Shapiro et al.

(10) Patent No.: US 9,895,353 B2
(45) Date of Patent: Feb. 20, 2018

(54) USE OF L-TRYPTOPHAN FOR THE TREATMENT OF PARASOMNIAS

(71) Applicant: Zzeemag Inc., Toronto (CA)

(72) Inventors: Colin Shapiro, Toronto (CA); Louis Van Zyl, Toronto (CA)

(73) Assignee: Zzeemag Inc., Toronto, ON (CA)

( * ) Notice: Subject to any disclaimer, the term of this patent is extended or adjusted under 35 U.S.C. 154(b) by 0 days.

(21) Appl. No.: 15/021,122

(22) PCT Filed: Sep. 10, 2014

(86) PCT No.: PCT/CA2014/000677
§ 371 (c)(1),
(2) Date: Mar. 10, 2016

(87) PCT Pub. No.: WO2015/035500
PCT Pub. Date: Mar. 19, 2015

(65) Prior Publication Data
US 2016/0220533 A1    Aug. 4, 2016

Related U.S. Application Data

(60) Provisional application No. 61/876,545, filed on Sep. 11, 2013.

(51) Int. Cl.
*A61K 31/405* (2006.01)
*A61K 9/08* (2006.01)

(52) U.S. Cl.
CPC .............. *A61K 31/405* (2013.01); *A61K 9/08* (2013.01)

(58) Field of Classification Search
USPC .......................................................... 514/217
See application file for complete search history.

(56) References Cited

U.S. PATENT DOCUMENTS

| 5,691,324 A | 11/1997 | Sandyk |
| 2009/0104171 A1 | 4/2009 | Pardee et al. |
| 2011/0288145 A1 | 11/2011 | Kamprad |
| 2012/0237570 A1 | 9/2012 | Crain et al. |

FOREIGN PATENT DOCUMENTS

| EP | 1743633 A1 | 1/2007 |
| WO | 2011/018700 A1 | 2/2011 |

OTHER PUBLICATIONS

Bruni et al., Eur J Oediatr., 2004;163:402-407.*
Fernstrom, Physiological Reviews, 1983;63(2):484-546.*
(Continued)

*Primary Examiner* — San Ming R Hui
(74) *Attorney, Agent, or Firm* — Bereskin & Parr LLP/S.E.N.C.R.L., s.r.l.; I. Laurence MacPhie

(57) ABSTRACT

Described is the use of L-tryptophan for treating a subject with parasomnia and associated methods of treating a subject with parasomnia. Optionally, the subject may be a child or adolescent between about 3 years of age and 18 years of age. The methods and uses described herein are useful for treating parasomnia in a subject exhibiting sleep walking, sleeptalking, confusional arousals, nightmares, night terrors, rhythmic movement disorder, sleep related eating disorder and/or bruxism. Optionally, subjects are treated with a dose L-tryptophan of about between 700 mg and 5 g per day.

21 Claims, 1 Drawing Sheet

(56) References Cited

OTHER PUBLICATIONS

Parasomnia, Aug. 2011, https://sleepmedicineboardreview.wordpress.com/category/parasomnias/.*

Harding, Better Brain Chemistry with Tryptophan, Life Extension Magazine, May 2013, from http://www.lifeextension.com/Magazine/2013/5/Better-Brain-Chemistry-with-Tryptophan/.*

Brown, C.C., et al., "Effects of L-Tryptophan on sleep-onset insomniacs." Waking Sleeping, 1979, vol. 3, Issue 2, pp. 101-108. (Abstract Only).

Brunt, O., et al., "L-5-HydroxyL-Tryptophan treatment of sleep terrors in children." Eur J Pediatr, 2004,163, pp. 402-407.

Bloomfield, E.R., and Shatkin, J.P., "Parasomnias and Movement Disorders in Children and Adolescents." Child Adolesc Psychiatric Clin N Am, 2009, 18, pp. 947-965.

Sole, J.O., et al., "L-Tryptophan: clinical studies. In: Cole, J.O. (Ed.), Psychopharmacology Update." The Collamore Press, Lexington, Massachusetts, 1980, pp. 119-148.

Etzel, K.R., et al., "L-Tryptophan supplementation for nocturnal bruxism: report of negative results." J Craniomandib Disord, 1991, 5(2), pp. 115-120. (Abstract Only).

Hartmann, E., et al., "Hypnotic effects of L-Tryptophan." Arch Gen Psychiatry, 1974, vol. 31, pp. 394-397.

Hartmann, E., and Spinweber, C.L., "Sleep induced by L-Tryptophan: effect of dosages within the normal dietary intake." J Nero Ment Dis, 1979, vol. 167, No. 8, pp. 497-499.

Hartmann, E., and Greenwald, D., "L-Tryptophan and human sleep: an analysis of 43 studies. In: Schlossberger, H.G., Kochen, W., Linzen, B., Steinhart, H. (Eds.), Progress in L-Tryptophan and Serotonin Research." Walter de Gruyter, Berlin, 1984, pp. 297-304.

Hedaya, K.J., "Pharmacokinetic factors in the clinical use of L-Tryptophan." Journal of Clinical Psychopharmacology, 1984, vol. 4, No. 6, pp. 347-348.

Klackenberg, G., "Incidence of Parasomnias in children in a general population." In: Guilleminault C, editor. Sleep and its disorders in children. New York: Raven Press, 1987, pp. 99-113.

Levitan, R.D., et al., "Preliminary randomized double-blind placebo-controlled trial of L-Tryptophan combined with fluoxetine to treat major depressive disorder: antidepressant and hypnotic effects." J Psychiatry Neurosci., 2000, vol. 25, No. 4, pp. 337-346.

Petit, D., et al., "Dyssomnias and Parasomnias in early childhood." Pediatrics, 2007, vol. 119, No. 5, pp. 1016-1025.

Riemann, D., et al., "The L-Tryptophan depletion test: impact on sleep in primary insomnia—a pilot study." Psychiatry Res, 2002, 109, pp. 129-135.

Sainio, E.L., et al., "L-Tryptophan: Biochemical, nutritional and pharmacological aspects." Amino Acids, 1996, 10, pp. 21-47.

Schneider-Helmert, D., and Bodmer, M., "Definitive recovery from chronic severe insomnia by long term interval therapy with L-Tryptophan." Sleep Res, 1983, 12, p. 126.

Snyder, S. and Iiams, G., "Serotonergic agents in the treatment of isolated sleep paralysis." American Journal of Psychiatry, 1982,139:9, pp. 1202-1203.

Sours, J.A., et al., "Somnambulism: Its Clinical Significance and Dynamic Meaning in Late Adolescence and Adulthood." Arch Gen Psychiatry, 1963, 9, pp. 400-413.

Young, S.N., "The clinical psychopharmacology of L-Tryptophan." Nutrition and the Brain: Food Constitutes Affecting Normal and Abnormal Behaviors, New York: Raven Press, 1986, vol. 7, pp. 49-88.

Wyatt, R.J., et al., "Effects of L-Tryptophan (a natural sedative) on human sleep." Lancet, 1970, 2, pp. 842-846.

Written Opinion and International Search Report for corresponding PCT Application No. PCT/CA2014/000677 both completed dated Dec. 12, 2014.

Sandyk, R., "L-Tryptophan in the Treatment of Restless Legs Syndrome." American Journal of Psychiartry, 1986, vol. 143(4).

De Giogis, G., et al., "Headache in association with sleep disorders in children: a psychodiagnostic evaluation and controlled clinical study-L-5-HTP versus placebo." Drugs Exptl. Clin. Res., 1967, vol. XIII(7), pp. 425-433.

Brunt, O., and Novelli, L., "Sleep Disorders in Children." Clinical Evidence, 2010, 09, 2304.

Fernstrom, J.D., "Role of Precursor Availability in Control of Monoamine Biosynthesis in Brain." Physiological Reviews, Apr. 1983, vol. 63, No. 2, pp. 484-546.

* cited by examiner

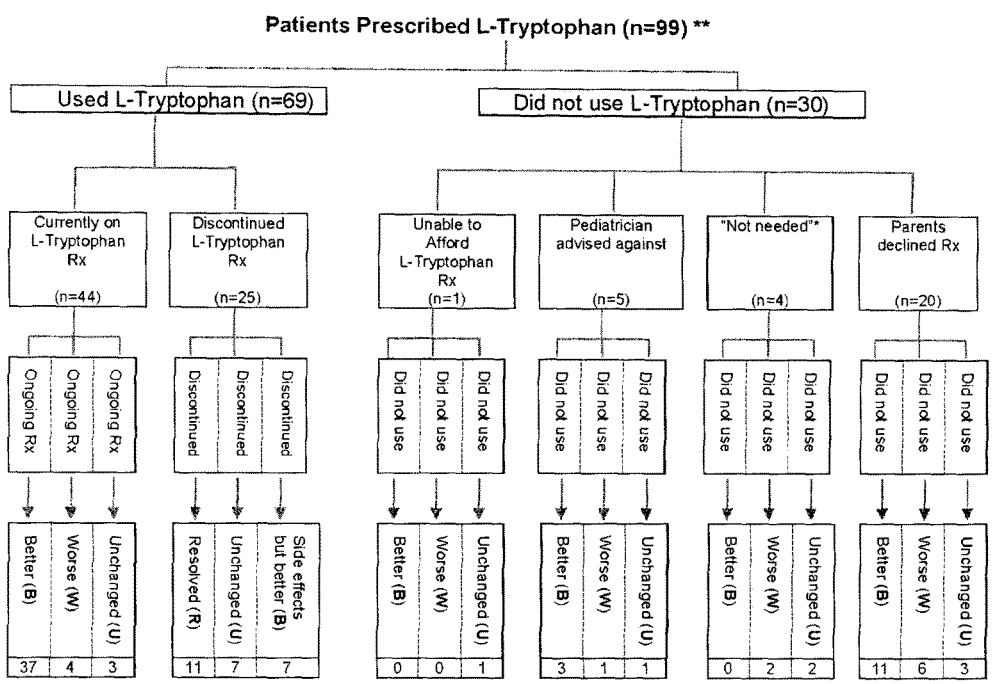
Rx, Prescription
B – Got better, W – Got worse, R – Spontaneously Resolved, U - Unchanged (i.e., there were no changes in symptom frequency).
* Medication not needed based on clinical judgement and parent preference
** An additional 8 patients were prescribed L-Tryptophan but were lost to follow-up.

USE OF L-TRYPTOPHAN FOR THE TREATMENT OF PARASOMNIAS

CROSS REFERENCE TO RELATED APPLICATIONS

This application is a national phase entry of PCT/CA2014/000677 filed Sep. 10, 2014 (which designates the U.S.) which claims priority to U.S. Provisional Application Ser. No. 61/876,545, filed on Sep. 11, 2013, the entire contents of which are hereby incorporated by reference.

FIELD

The present disclosure relates to parasomnias and more specifically to the use of L-tryptophan for the treatment of parasomnias.

INTRODUCTION

Parasomnias are a category of disruptive sleep disorders characterized by the occurrence of abnormal and unwanted movements and behaviours during sleep, between sleep stages, or during arousal from sleep. Sleepwalking, sleep-talking, night terrors and other parasomnias are quite common in childhood. In many instances specific intervention is not required, although in frequent and severe cases there are injury risks, problems associated with sleep deprivation and general disruption to the family unit. Pharmacological treatment of sleep disorders can bring with it unwanted side effects such as fatigue and cognitive impairment, as well as tolerance, dependence and withdrawal. These issues can make it particularly unsuitable for treatment of children.

Sleep plays a critical role in maintaining the psychological health of children, with sleep deficiencies correlating with depression, hopelessness, and lowered self-esteem (Bloomfield and Shatkin, 2009). Thus, parasomnias are serious clinical disorders that may result in serious physical injury, sleep disruption, and adverse health and psychosocial effects.

The prevalence of parasomnias is high from infancy to adolescence, and occasionally continues into adulthood. In a longitudinal, population-based survey, Klackenberg (1987) found that up to 45% of children aged 4-16 years had experienced sleep walking and 3.5% of this group also met criteria for sleep terrors. More recently, Petit et al. (2007) followed approximately 1000 subjects between the ages of 2.5 years and 6 years, and the overall prevalence of each parasomnia for the period studied was as follows: sleep-walking (14.5%), sleep terrors (39.8%), sleeptalking (84.4%), enuresis (25.0%), bruxism (45.6%) and rhythmic movements (9.2%). In this study 88% of the cohort manifested at least one parasomnia during the study period.

L-tryptophan is an essential dietary amino acid and the metabolic precursor for some of the hormones and neurotransmitters fundamental for sleep-wake circuit synchrony. L-tryptophan has long been recognized for its sleep-inducing properties and as the natural amino acid precursor for serotonin biosynthesis, the effects of L-tryptophan on sleep are presumed to be through the serotonergic system, which is intrinsically linked to sleep, arousal and motor control.

Most of the research into L-tryptophan's has focused on its effects on the various parameters of sleep architecture as well as its apparent sleep-inducing or somnogenic properties and potential utility for the treatment of insomnia. Using techniques like acute L-Tryptophan depletion (ATD), L-Tryptophan loading and others, the results have been somewhat variable with the consensus of reviews stating that it can be an effective hypnotic under some circumstances (see e.g. Young, 1986; Hartmann and Greenwald, 1984). While not as effective as pharmaceutical hypnotics in treatment of severe insomnia, it has been shown to decrease sleep latency by about half in mild insomnia at lower doses (<4 g) without altering sleep architecture (Sainio et al., 1996).

There remains a need for novel treatments of parasomnia and in particular for novel treatments of parasomnia suitable for children.

SUMMARY

The present disclosure describes the use of L-tryptophan for use in the treatment of parasomnias. It has surprisingly been determined that L-tryptophan is useful for treating parasomnias. While the somnogenic properties of L-tryptophan are well known, the applicants are not aware of any previous studies reporting the use of L-tryptophan for the treatment of parasomnias. As set out in Example 1, in a sample of 165 subjects diagnosed with parasomnia, including sleep walking, sleep talking, nightmares and night terrors, 80% of the subjects who were administered L-Tryptophan showed significant improvement of symptoms.

The use of L-tryptophan for the treatment of parasomnias provides a number of advantages over existing therapies and pharmacological treatments. For example, the use L-tryptophan for the treatment of parasomnias may also be better received and tolerated by subjects concerned about of the use of medications and in particular subjects concerned about the use medications in children and/or adolescents. L-tryptophan presents fewer or no side effects compared to the use of traditional pharmacotherapies for the treatment of parasomnias, such as clonazepam. The use of L-tryptophan for treating parasomnia may also present additional advantages compared to the use of metabolites such as L-5-HTP, including metabolic effects on vitamin metabolism. L-trypotophan also has the advantage of being a natural substance which is also present in a number of foodstuffs such as cheese, milk and meat and fish.

Accordingly, in one aspect of the present disclosure there is provided a method of treating a subject with parasomnia, the method comprising administering to the subject a therapeutically effective amount of L-tryptophan. In one embodiment, the subject with parasomnia exhibits sleep walking, sleeptalking, confusional arousals, nightmares, night terrors, rhythmic movement disorder, sleep related eating disorder and/or bruxism. In one embodiment, the rhythmic movement disorder comprises restless leg syndrome and/or periodic limb movements.

In one embodiment, L-tryptophan is administered orally to the subject or formulated for use as an oral medicament or an oral composition. In one embodiment, L-tryptophan is administered or used in the evening, such as before going to bed or before a period of sleep. In one embodiment, L-tryptophan may be administered or used daily or periodically by the subject. In one embodiment, L-tryptophan may be administered or is formulated for use as a solution, in pill form, or as a capsule.

In one aspect of the disclosure, L-tryptophan has been determined to be particularly useful for the treatment of parasomnias in children and/or adolescents. For example, in one embodiment the methods and uses described herein are for the treatment of parasomnia in subjects less than about 19 years of age. In one embodiment, the methods and uses described herein are for the treatment of parasomnia in a child, optionally a subject between about 3 years of age and about 12 years of age. In one embodiment, the methods and uses described herein are for the treatment of parasomnia in an adolescent, optionally a subject between about 13 years of age and about 18 years of age. In one embodiment the methods and uses described herein are for the treatment of parasomnia in an adult, optionally a subject greater than about 19 years of age.

In one embodiment, a therapeutically effective dose of L-tryptophan is administered or used by the subject for the treatment of parasomnia. For example, in one embodiment, the dose of L-tryptophan is between about 700 mg to about 5000 mg per day. In one embodiment, the subject is a child, and the dose of L-tryptophan is from about 350 mg to about 2500 mg. In one embodiment, the subject is an adolescent, and the dose of L-tryptophan is from about 700 mg to about 3500 mg. In one embodiment, the subject is an adult, and the dose of L-tryptophan is from about 700 mg to about 5000 mg. In one embodiment, the subject is a child, an adolescent or an adult and the dose of L-tryptophan is about 2250 mg. Optionally, the dose of L-tryptophan is administered or used daily. In one embodiment, the dose is about 500 mg, 600 mg, 700 mg, 800 mg, 900 mg, 1000 mg, 1500 mg, 2000 mg, 2500 mg, 3000 mg, 3500 mg, 4000 mg, 4500 mg, or 5000 mg.

In one embodiment, the methods and uses described herein for the treatment of parasomnia with L-tryptophan reduce the frequency of parasomnic events in the subject. In one embodiment, the methods and uses described herein for the treatment of parasomnia with L-tryptophan reduce the severity of parasomnic events in the subject. In one embodiment, the methods and uses described herein for the treatment of parasomnia with L-tryptophan reduce the frequency of intermittent arousals during slow-wave sleep (SWS) in the subject.

Also provided is L-tryptophan for use in the treatment of parasomania or a pharmaceutical composition comprising L-tryptophan for use in the treatment of parasomnia as described herein. Also provided is the use of L-tryptophan in the manufacture of a medicament or a pharmaceutical composition for the treatment of parasomnia as described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the disclosure will now be described in relation to the drawings in which:

FIG. 1 shows a flowchart tracing the outcome of subjects that were prescribed L-tryptophan as set out in Example 1. 99 were prescribed L-Tryptophan. Of the 69 patients who took L-Tryptophan (n=69): an improvement in parasomnia symptoms (B or R) was observed in 55 (80%); worsening of parasomnia symptoms (W) was observed in 4 (6%); and no change in parasomnia symptoms (U) was observed in 10 (14%). Of the 30 patients who did not take L-Tryptophan (n=30): spontaneous improvement in parasomnia symptoms (B) was observed in 14 (47%); worsening of parasomnia symptoms (W) was observed in 9 (30%); and no change in parasomnia symptoms (U) was observed in 7 (23%). Side Effects were observed in 7 out of 69 (10%). ** An additional 8 patients were prescribed L-Tryptophan but were lost to follow-up.

DETAILED DESCRIPTION

Definitions

As used herein, "L-tryptophan" refers to the essential amino acid commonly known in the art also known as (2S)-2-amino-3-(1H-indol-3-yl)propanoic acid. Preparations of L-tryptophan for use in the methods described herein may optionally contain some amount of the D stereoisomer. Optionally, preparations of L-tryptophan may contain more than 50%, 80%, 90%, 95%, 99%, or greater than 99% of the L-stereoisomer. The distinguishing structural characteristic of L-tryptophan, the indole ring, remains conserved when metabolized into two of the principal agents of sleep-wake regulation, the neurosecretory hormone melatonin and the neurotransmitter serotonin. The metabolism of L-tryptophan also serves as a precursor to many substances including niacin, quinolinic acid (involved in gluconeogenesis), picolinic acid (involved in the absorption of zinc), coenzyme NAD+, kynurenic acid (KYNA).

As used herein, "parasomnia" or "parasomnias" refers to disorders characterized by abnormal behavioral or physiological events occurring in association with sleep, specific sleep stages, or sleep-wake transition. In some embodiments, parasomnia includes sleepwalking, sleeptalking, night terrors, enuresis, restless leg syndrome (RLS), bruxism and other undesirable, non-deliberate events accompanying sleep, or any combination thereof. In one embodiment, parasomnia may be grouped into three categories as per the International Classification of Sleep Disorders, second edition (ICSD-2): 1) Disorders of arousal from NREM sleep, which includes sleepwalking, sleep terrors and confusional arousals, 2) Parasomnias usually associated with REM sleep, which includes nightmares and, 3) Other Parasomnias, which includes sleep enuresis, sleep-related eating disorder, sleep-related hallucinations, sleep-related groaning and several others. In one embodiment, the methods and uses described herein are useful for the treatment of subjects who exhibit one or more abnormal behavioral or physiological events such as sleep walking, sleeptalking, confusional arousals, nightmares, night terrors, rhythmic movement disorder, sleep related eating disorder and/or bruxism. In one embodiment, the methods and uses described herein are useful for the treatment of subjects who exhibit one or more movement disorders, such as rhythmic movement disorder, restless leg syndrome and/or periodic limb movements in sleep.

As used herein, the phrase "effective amount" or "therapeutically effective amount" means an amount effective, at dosages and for periods of time necessary to achieve the desired result. For example in the context of treating parasomnia, an effective amount is an amount that, for example, reduces the frequency and/or severity of abnormal behavioral or physiological events associated with parasomnias compared to the response obtained without administration of the compound. Effective amounts may vary according to factors such as the disease state, age, sex and weight of the subject. The amount of L-tryptophan that will correspond to such an amount will vary depending upon various factors, such as the pharmaceutical formulation, the route of administration, the identity of the subject being treated, and the like, but can nevertheless be routinely determined by one skilled in the art.

The term "subject" as used herein includes all members of the animal kingdom including mammals, and suitably refers to humans.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of the disorder, stabilized (i.e. not worsening) state of disorder, amelioration or palliation of the disorder state, whether detectable or undetectable. "Treating" and "treatment" as used herein also include prophylactic treatment. In one embodiment, treatment methods comprise administering to a subject a therapeutically effective amount of L-tryptophan as described herein and optionally consists of a single administration or use, or alternatively comprises a series of administrations or uses. In one embodiment, treating a subject with parasomnia reduces the frequency and/or severity of abnormal behavioral or physiological events associated with parasomnias compared to the response obtained without the use or administration of L-tryptophan.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods and Uses of L-Tryptophan for the Treatment of Parasomnia

In one aspect, the present disclosure provides methods for and associated uses for treating parasomnias. As set out in Example 1, 80% of subjects diagnosed with parasomnia who were treated with L-tryptophan showed a significant improvement of symptoms. Furthermore, as set out in Example 2, a detailed analysis of a series of subjects presenting with parasomnia demonstrates that L-tryptophan is useful for the treatment or a variety of abnormal behavioral or physiological events associated with parasomnia including sleep terrors, sleep talking, bed wetting/enuresis, sleep walking, movement disorders and bruxism.

Accordingly, in one aspect there is provided a method of treating a subject with parasomnia. In one embodiment, the method comprises administering to the subject a therapeutically effective amount of L-tryptophan. Also provided is the use of a therapeutically effective amount of L-tryptophan for the treatment of parasomnia in a subject in need thereof.

In one embodiment, the methods and uses described herein are for the treatment of parasomnia in a subject less than about 20, 19, 18, 17, 16 or 15 years of age. Optionally, the methods and uses described herein are for the treatment of parasomnia in a subject who has not yet reached puberty. In one embodiment, the methods and uses described herein are for the treatment of parasomnia in a subject who is a child or adolescent. For example, in one embodiment, the child is a subject with parasomnia between about 3 years of age and about 12 years of age. In one embodiment, the methods and uses described herein are for the treatment of parasomnia in an adolescent. For example, in one embodiment, the adolescent is a subject between about 13 years of age and 17 years of age.

In one embodiment, the methods and uses described herein are also useful for the treatment of parasomnia in an adult. For example, in one embodiment, the adult is a subject greater than about 18, 19, 20 or 21 years of age.

In one aspect, the methods and uses described herein are useful for the treatment of parasomnia and the different abnormal behavioral or physiological events associated with parasomnia. For example, in one embodiment L-tryptophan is useful for treating subjects who exhibit sleep terrors and/or night terrors, sleep talking, bed wetting/enuresis, sleep walking, unwanted movement disorders, bruxism and other undesirable, non-deliberate events accompanying sleep, or any combination thereof. In one embodiment, L-tryptophan is useful for treating subjects who exhibit unnatural or unwanted movements during sleep, such as rhythmic movement disorders, restless leg syndrome (RLS) and/or periodic limb movements.

In on embodiment, L-tryptophan is useful for the treatment of parasomnia associated with disorders of arousal from NREM sleep, such as sleepwalking, sleep terrors and/or confusional arousals. In one embodiment, L-tryptophan is useful for the treatment of parasomnia associated with REM sleep, such as nightmares. In one embodiment, L-tryptophan is useful for the treatment of parasomnia associated with other abnormal behavioral or physiological events such as sleep enuresis, sleep-related eating disorder, sleep-related hallucinations and sleep-related groaning.

As shown in Example 2, the use of L-tryptophan is also useful for treating subjects that present with a plurality of abnormal behaviors or physiological events associated with parasomnia. For example, in one embodiment L-tryptophan is useful for treating subjects who present with at least two abnormal behaviors or physiological events selected from sleep walking, sleeptalking, confusional arousals, nightmares, sleep terrors, unwanted movement disorders, and bruxism.

A person skilled in the art will appreciate that the dose of L-tryptophan to be used in the treatment of a subject with parasomnia will depend on a number of factors including, but not limited to, the age of the subject, weight, tolerance to L-tryptophan and severity of symptoms. A person skilled in the art will readily be able to determine a therapeutically effective dose for a subject presenting with parasomnia. For example, in one embodiment, subjects are administered an oral dose of L-tryptophan of less than about 5 grams of per day. In one embodiment, the dose of L-tryptophan is between about 700 mg to about 5000 mg. In children, a typical oral dose of L-tryptophan for the treatment of parasomnia is from about 350 mg to about 2500 mg per day. In adolescents, the dose of L-tryptophan may be from about 700 mg to about 3500 mg, while in adults, the dose may be from about 700 mg to about 5000 mg. In a preferred embodiment, the dose of L-tryptophan is an oral dose of 2000-2500 mg, and optionally 2250 mg or 2220 mg, typically a daily dose. In one embodiment, L-tryptophan is administered or used in the evening before bed. For example, in one embodiment, L-tryptophan is administered or used within 2 hours, 1 hour, 30 minutes or less than 30 minutes before the subject goes to sleep. In a preferred embodiment, L-tryptophan is administered or used about 1 hour before the subject goes to sleep.

L-tryptophan can be formulated for administration or use by a subject as commonly known in the art. For example, in one embodiment L-tryptophan is combined with one or more pharmaceutically acceptable carriers. In one embodiment, L-tryptophan is administered or is formulated for use as a solution, in pill form, or as a capsule. In one embodiment, the dose of L-tryptophan is about 500 mg, 600 mg, 700 mg, 800 mg, 900 mg, 1000 mg, 1500 mg, 2000 mg, 2100 mg, 2200 mg, 2250 mg, 2300 mg, 2400 mg, 2500 mg, 3000 mg, 3500 mg, 4000 mg, 4500 mg, or 5000 mg.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1: Retrospective Study of Subjects with Parasomnia

A retrospective study was performed to evaluate the effects of L-tryoptophan on subjects with parasomnia and to look for sleep architectural differences in children before and after treatment.

Using a sample of 165 patients diagnosed with Parasomnia, including sleep walking, sleep talking, nightmares and night terrors, 80% of the subjects who were administered L-tryptophan showed significant improvement of symptoms. L-tryptophan is therefore an effective option in the management of parasomnias with the added advantage of the absence of side effects associated with traditional pharmacotherapy.

Materials and Methods

Confidential charts were selected of boys and girls between the ages of 3 and 18 years with a clinical diagnosis of Parasomnias, and including behaviours of sleep walking, sleep talking, nightmares or night-terrors.

The 165 subjects that were included in the retrospective study of confidential charts were prescribed treatment with L-Tryptophan or Clonazepam, or no treatment. The exclusion criteria were children under the age 3 years or over the age 18 years and those undergoing treatment for Parasomnia at the time of the sleep study.

The diagnosis of parasomnia was made by a sleep physician and based on the clinical history together with confirmation from the polysomnographic sleep study findings.

An overnight polysomnographic sleep study and questionnaire data were collected during this study for each subject. Each of the subjects at the sleep clinic responded to a battery of questionnaires consisting of: Pediatric Daytime Sleepiness Scale (PDSS), THAT alertness scale, SNAP assessment for ADHD symptoms, Centre for Epidemiologic Studies in depression scale modified for children (CES-DC), and SCARED anxiety scale.

A follow-up questionnaire was formulated to assess for their symptoms following treatment with Tryptophan to compare values before and after treatment. A follow-up phone interview was conducted to assess the frequency of Parasomnias during and after treatment. The follow-up questionnaire included: daytime sleepiness, level of attention and concentration, ability to wake up in the morning, number of hours of sleep at night and incidence of temper tantrums.

Results

The results of the group were divided by gender. Group averages for the sleep architectural variables and scores on the questionnaires were compared to normative values. In order to facilitate the comparison with normative values patients were divided by gender and age groups as follows: 3-5, 6-9, 10-12, 13-15 and 16-18 years.

Data from 106 (65%) boys and 59 (35%) girls with diagnosed parasomnia were included in the study. The average age of children was 10±4 years; boys 10±4 years (range 3-18) and girls 11±4 years (range 4-18). Sleep architectural values for each of the subjects in the study are presented in Table 1.

TABLE 1

Sleep Architectural Variables Mean values for the sleep architectural variables are grouped by gender and age.

| | TST (min) | SOL (min) | Total AI | S1 (%) | S2 (%) | SWS (%) | REM (%) | Wake (%) | SE (%) |
|---|---|---|---|---|---|---|---|---|---|
| Males: | | | | | | | | | |
| 3-5 | 523.6 | 29.3 | 10.1 | 4.0 | 41.4 | 28.4 | 20.4 | 5.5 | 88.2 |
| SD | 38.6 | 18.2 | 2.9 | 2.3 | 10.2 | 7.9 | 5.2 | 3.2 | 4.6 |
| 6-9 | 512.5 | 22.6 | 9.4 | 4.5 | 38.2 | 27.7 | 21.8 | 7.2 | 88.4 |
| SD | 41.5 | 17.9 | 2.9 | 2.1 | 5.0 | 5.3 | 4.5 | 5.9 | 6.4 |
| 10-12 | 485.8 | 30.7 | 9.8 | 4.9 | 40.7 | 24.3 | 19.6 | 9.3 | 84.8 |
| SD | 66.5 | 31.3 | 3.6 | 2.5 | 8.9 | 4.5 | 5.7 | 8.4 | 10.2 |
| 13-15 | 453.3 | 32.7 | 14.3 | 5.0 | 43.6 | 22.6 | 19.1 | 6.8 | 78.0 |
| SD | 64.3 | 38.7 | 12.3 | 2.3 | 11.0 | 5.3 | 4.9 | 5.4 | 25.6 |
| 16-18 | 479.1 | 9.1 | 14.9 | 4.2 | 47.9 | 19.4 | 22.9 | 4.2 | 71.7 |
| SD | 22.9 | 5.7 | 6.5 | 1.8 | 8.9 | 8.8 | 7.6 | 3.1 | 47.2 |
| Females: | | | | | | | | | |
| 3-5 | 550.4 | 31.2 | 10.1 | 4.5 | 39.4 | 30.3 | 20.0 | 5.4 | 89.5 |
| SD | 34.2 | 28.9 | 2.1 | 2.3 | 6.5 | 6.5 | 5.5 | 5.9 | 7.0 |
| 6-9 | 494.9 | 43.4 | 10.6 | 5.1 | 39.4 | 24.5 | 18.2 | 11.9 | 82.3 |
| SD | 47.7 | 33.4 | 3.6 | 3.3 | 7.5 | 5.8 | 6.2 | 7.6 | 8.5 |
| 10-12 | 469.6 | 46.3 | 8.2 | 3.5 | 40.9 | 28.9 | 18.9 | 7.2 | 84.0 |
| SD | 84.4 | 65.5 | 3.7 | 1.6 | 9.2 | 6.9 | 5.8 | 9.3 | 14.0 |
| 13-15 | 451.1 | 32.8 | 10.5 | 6.0 | 46.5 | 18.3 | 21.5 | 7.1 | 86.6 |

TABLE 1-continued

Sleep Architectural Variables Mean values for the sleep architectural variables are grouped by gender and age.

|       | TST (min) | SOL (min) | Total AI | S1 (%) | S2 (%) | SWS (%) | REM (%) | Wake (%) | SE (%) |
|-------|-----------|-----------|----------|--------|--------|---------|---------|----------|--------|
| SD    | 51.8      | 29.7      | 5.4      | 2.8    | 7.1    | 4.4     | 5.9     | 7.0      | 9.9    |
| 16-18 | 433.6     | 30.5      | 11.6     | 4.0    | 51.7   | 15.3    | 16.5    | 12.1     | 59.1   |
| SD    | 82.7      | 30.2      | 3.4      | 1.6    | 8.8    | 8.3     | 7.3     | 18.0     | 42.4   |

Standard deviations (SD) are listed below each mean. TST, total leep time; SOL, sleep onset latency; AI, arousal index; S1, stage 1 sleep; S2, stage 2 sleep; SWS, slow wave sleep; REM, rapid eye movement sleep; SE, sleep efficiency.

As shown in Table 2, a number of children with parasomnias have elevated sleep onset latency, elevated arousal index and reduced total sleep time, combined with fragmented sleep, increased wake time and a greater number of arousals.

TABLE 2

Summary of abnormalities in sleep architectural variables in children with parasomnias.

|                      |          | MALES (age ranges) | FEMALES (age ranges) |
|----------------------|----------|--------------------|----------------------|
| Total Sleep Time     | Reduced  | 13-15              | 10-18                |
| Sleep Onset Latency  | Elevated | 10-15              | 3-18                 |
| Arousal Index        | Elevated | 13-18              | 16-18                |
| Stage 1 %            | Elevated | 3-15               | 3-15                 |
| Stage 2 %            | Reduced  | 3-12               | 3-15                 |
| Slow Wave Sleep %    | Elevated | 3-12               | 3-12                 |
|                      | Reduced  | 13-18              | 13-18                |
| REM %                | Reduced  | 3-15               | 3-18                 |
| Wake %               | Elevated | 3-18               | 3-18                 |
| Sleep Efficiency %   | Reduced  | 3-18               | 3-18                 |

In addition, 29% (n=17) of girls and 44% (n=44) of boys were found to have mild obstructive sleep apnea (OSA) (AHI>1.5, <5) and 1 girl and 3 boys had moderate (AHI>5, <10) OSA. Lastly, 2 girls and 6 boys were found to have elevated periodic limb movements (PLMs) with a PLM index >5.

Based on the questionnaires, both girls and boys with parasomnia were found to have increased symptoms of depression and fatigue based on established the cut-off scores for the CES-DC and FSS scales (Table 3).

TABLE 3

Summary of questionnaire data on subjects with parasomnia.

|             | PDSS | FSS   | CES-D | SNAP | SCARED | THAT |
|-------------|------|-------|-------|------|--------|------|
| Males       | 14.1 | 3.9*  | 17.9* | 1.7  | 19.8   | 24.7 |
| Females     | 14.3 | 3.1*  | 17.6* | 1.1  | 20.3   | 25.9 |
| Cutoff Value| >17  | >2.3  | >15   | >2   | >25    | <20  |

Ninety nine (60%) of the 165 children were prescribed L-tryptophan to manage their parasomnia. The remaining were either prescribed Clonazepam (n=32) or were not prescribed anything. The latter reflected parental preference and/or clinical judgement. FIG. 1 is a flowchart of the outcome of children who took or did not take L-tryptophan.

As shown in Table 4, the vast majority (80%) of children prescribed L-tryptophan who followed through with treatment saw improvements in their parasomnia symptoms compared to less than half (47%) of those not taking Tryptophan. Further, compared to those on Tryptophan treatment, five times as many (30% versus 6%) of those not taking Tryptophan experienced a worsening of symptoms. Lastly, over half as many (23% versus 14%) of those not on treatment saw no improvement in symptoms when compared to those taking Tryptophan.

TABLE 4

Summary of the effects of treatment with L-tryptophan on subjects with parasomnia. An additional 8 patients were prescribed and treated with L-Tryptophan, but were lost to follow-up.

|             | L-Tryoptophan | No L-Tryptophan |
|-------------|---------------|-----------------|
| Improvement | 55(80%)       | 14 (47%)        |
| Worsening   | 4(6%)         | 9(30%)          |
| No Change   | 10(14%)       | 7(23%)          |

Discussion

The findings of the present study confirm that parasomnias in children are not benign and treatment is warranted. In the present study there were 14 children who refused treatment and who did not outgrow parasomnias. These children have experienced poor sleep and academic performance.

Consolidation of sleep through treatment with L-tryptophan reduced the frequency of parasomnic events in children notably through decreasing the number of arousals in sleep. Subjects who were administered L-tryptophan also experienced a reduced number of temper tantrums, increased alertness and better attention during the day.

Without being limited by theory, the therapeutic effects of L-tryptophan on parasomnia may be through stimulation of the serotonergic system, which is highly involved in the regulation of sleep and motor control. parasomnias are most commonly associated with the slow wave sleep (SWS) stage of sleep. During this stage the raphe nuclei, which synthesize and project serotonin to the other areas of the brain, are in an intermediate stage of activity, that is, not as active as during wakefulness and not as disengaged as during REM sleep. This intermediate level of serotonin activity during SWS creates a situation of vulnerability to serotonin fluctuation, whereby too much could tip the balance of sleep into wakefulness and too little could facilitate REM sleep. Bearing this in mind, serotonin must be precisely monitored and accurately released in order to maintain the stage of SWS. This serotonergic balance is performed primarily through $5\text{-HT}_{1a}$ receptors, which, depending on their distribution, can increase serotonin tone (if they are post-synaptic) or decrease (if they are located presynaptically).

The raphe nuclei along with the SCN are structures that are profoundly influenced by the serotonergic system. Both have been shown to generate delta waves associated with SWS. Activated CPGs responsible for SWS and production of delta waves are also involved in the stereotypic behaviours seen in parasomnias, such as sleepwalking, rhythmic movement disorder, bruxism, and others. These CPGs are tightly regulated by serotonin as well as GABA, which generally shows an inhibiting effect on serotonergic firing.

While the biochemical pathways that regulate sleep are complex, the effects of L-tryptophan on parasomnia may be through the serotonergic system that generates the circuit synchrony needed for sleep and motor control. L-Tryptophan's ability to reduce the amount of intermittent arousals during SWS could be mediated by stabilization of serotonin levels producing a more uniform sleep microstructure.

Example 2: Case Studies of Subjects Treated with L-Tryptophan for Parasomnia

A detailed analysis of a number of subjects presenting with parasomnia who were treated with L-tryptophan was performed. A selection of case reports of subjects treated with L-tryptophan are summarized below. Remarkably, L-tryptophan is useful for the treatment of subjects presenting with a variety of abnormal behavioral or physiological events occurring in association with sleep, specific sleep stages, or sleep-wake transition.

Case A: Somniloquy/Nightly Sleep Talking

Subject is a fourteen year old girl who was initially seen in consultation for assessment of excessive daytime sleepiness and fatigue. Her main complaint was that irrespective of how much she slept, she remained fatigued and sleepy during most of her wakeful hours.

History was obtained of her experiencing night terrors as a child and sleepwalking, and currently almost nightly sleep talking. Subject "tosses and turns" much during her sleep. Her mother reports frequent incidents of subject crying out and talking in her sleep.

Subject does not have any other medical problems. She had psychiatric treatment for anxiety and depression in the past but was not taking any medications at the time of the visit. Subject's brother occasionally sleep-walked. No other family members have a history of Parasomnia. There was no evidence on polysomnography showing parasomnic events, but clinical history suggested that this patient has NREM Parasomnia.

Treatment was initiated with L-tryptophan and at her current dose of 1.75 mg the patient's sleep has improved and her daytime fatigue has become less problematic. Subject was pleased to mention that she was sleeping uninterruptedly on most nights and experienced increased quality of sleep. She usually falls asleep within 15-20 minutes of retiring to bed between 10:30 pm and 11:00 pm. Since starting L-tryptophan, her nightly sleep talking has ceased.

Case B: Sleep Terrors and Bedwetting

Subject is a six-year old girl referred for assessment regarding difficulty waking up in the morning, excessive daytime sleepiness, complaints of fatigue and nightly bedwetting. Subject's parents were concerned about their daughter's interrupted sleep and this led to her declining school performance and social withdrawal.

History was obtained that on nights when subject starting to "fuss" within sixty to ninety minutes after falling asleep had become more frequent. This "fussing" usually culminated in her screaming, trembling, talking in her sleep and sitting up in bed without subject being awake. These events lasted between five and fifteen minutes and could repeat two or three times during a three hour period. Subject had also started nightly bedwetting six months prior to her visit in October.

Polysomnography identified her with sleep fragmentation with compromised sleep quality and features of NREM arousal Parasomnia.

Treatment was initiated with L-Tryptophan 500 mg daily taken one hour before bedtime. The dose was gradually increased to 3 g daily. Subject was able to tolerate L-tryptophan six capsules (3 g) one hour before bedtime and would fall asleep within sixty to ninety minutes. There have been no night terrors and she has been sleeping mostly uninterruptedly until being woken by her parents between seven and seven-thirty am. She has not had any difficulty getting started in the morning and there have been no observation of daytime somnolence or fatigue since her current L-tryptophan dose had been reached. Unfortunately, she still continues to experience nightly enuretic episodes.

Case C: Sleepwalking and Sleeping Restlessly

Subject, a five-year old girl, was seen for assessment regarding sleepwalking and sleeping restlessly. Subject's parents voiced their concern over subject's perceived poor quality of sleep causing difficulties rising in the morning and subsequent tiredness during the day manifesting in her withdrawal from friends and activities.

History was obtained from subject's mother describing her little girl coming to their room between 3:00 am and 5:00 am and standing by her parents' bed not saying anything. Her parents believe that she was sleepwalking on those occasions. On other nights subject would wake two to three times a night and complain that she was unable to sleep. The patient's father used to sleepwalk as a child and this only ceased during his teenage years.

A nocturnal polysomnographic assessment identified features of NREM arousal Parasomnia and mild sleep fragmentation. Treatment was initiated with L-tryptophan 500 mg daily taken one hour before bedtime with a carbohydrate snack. The dose was to be gradually increased to 3 g daily.

Subject's mother reported a marked improvement in subject's sleep at a dosage of 2 mg L-tryptophan. Since treatment with L-tryptophan, subject has been sleeping uninterruptedly with no periods of intervening wakefulness after initial sleep onset on most nights. No observed parasomnic behaviours of sleepwalking have been noticed. Her daytime endurance has also improved significantly.

Case D: Bruxism, Sleepwalking and Sleep-talking

Subject is a seven-year old boy who was initially seen in consultation for assessment regarding interrupted sleep, bruxism, sleepwalking and sleep talking. The patient was a restless sleeper and experienced daytime somnolence.

History obtained from Subject's parents described the patient usually falling asleep by 7:50 pm. When his mother looked in on him around 11 pm. she would find him moving about the bed or talking in his sleep. He sleepwalked regularly, going to his parent's room and sitting on the edge of their bed talking while clearly not awake. Teachers at Subject's school had also alerted Subject's parents to his apparent tiredness during the day, high incidence of distractibility and inability to sustain focus.

Family history was non-contributory in relation to Subject's Parasomnias. Polysomnography identified fragmented sleep, bruxism, NREM arousal Parasomnia and mild daytime sleepiness Treatment was started on L-tryptophan 250 mg daily with direction to gradually increase the dose to 2 g. daily. Since taking 2 g L-tryptophan daily, Subject's bruxism has declined significantly. There have been no episodes of sleep walking and Subject has not been complaining of daytime fatigue or somnolence. Subject's mother was pleased to report that she has been given positive feedback from Subject's schoolteachers that he is now much better able to sustain focus in class than previously.

Case E: Enuresis, Sleepwalking and Sleeptalking

Subject is an eight-year old boy in grade three. He was referred for assessment regarding difficulty initiating sleep, sleep talking and persistent enuresis.

History was obtained from Subject's mother describing him sleepwalking and sleep talking, as well as moving about his bed to the extent that he frequently fell out of bed. He also experienced frequent enuretic episodes, up to five out of seven nights per week. Subject would wake up feeling tired and felt fatigued when attending school.

There is no family history of parasomnic behaviors other than in the Subject. He has Asthma and uses Flovent and Ventolin inhalers as required but does not have any other medical conditions.

A Polysomnographic study identified features suggestive of a NREM arousal parasomnia. Treatment was started with L-tryptophan, reaching optimal results at 4.5 g daily.

Subject's mother has expressed her joy and pleasant surprise at the improvement observed in her son since treatment with L-tryptophan. She reported that Subject was falling asleep quickly and was maintaining his seep. He no longer walked or talked in his sleep. The frequency of bedwetting has declined substantially and he appears to be less irritable and much happier during the day.

Case F: Sleep Terrors

Subject is a five-year old boy who was seen initially in consultation for assessment regarding sleep terrors and experiencing problems in school.

History obtained from Subject's mother detailed sleep terrors experienced by her son as two-year old toddler. These resolved spontaneously, only to reappear four months prior to their visit. Associated with the above night terrors were night sweats, sleep walking and sleep talking. As far as the patient's mother is aware, there was no family history of parasomnic behaviours. Subject underwent adenotonsilectomy two months earlier but did not suffer from any medical conditions. Polysomnographic findings identified NREM arousal Parasomnia and bruxism.

Subject was started on a trial of L-tryptophan 250 mg taken one hour before bedtime with a carbohydrate snack. The dose was to be gradually increased to 3 g daily. Subject tolerated L-tryptophan well and is currently on a dose of 2.25 mg daily. His mother reports that his sleep overall has improved noticeably. He is ready to go to bed by 8:00 pm whereas in the past there was some struggle to have him agree to go to bed. Subject has entered primary school and is settling well in his new school environment and seems to be happy.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Brown C C, Horrom N J, Wagman A M I. Effects of L-Tryptophan on sleep-onset insomniacs. *Waking Sleeping* 1979; 3:101-8.
Bruni O, Ferri R, Miano S, Verrillo E. L-5-HydroxyL-Tryptophan treatment of sleep terrors in children. *Eur J Pediatr* 2004; 163:402-7.
Bloomfield, E R, Shatkin, J P. Parasomnias and Movement Disorders in Children and Adolescents. *Child Adolesc Psychiatric Clin N Am* 2009; 18: 947-965.
Cole, J. O., Hartmann, E., Brigham, P., 1980. L-Tryptophan: clinical studies. In: Cole, J. O. (Ed.), Psychopharmacology Update. The Collamore Press, Lexington, Mass., pp. 119-148.
Etzel K R, Stockstill J W, Rugh J D, Fisher J G. L-Tryptophan supplementation for nocturnal bruxism: report of negative results. *J Craniomandib Disord* 1991:5:115-20.
Hartmann E, Cravens J, List S. Hypnotic effects of L-Tryptophan. *Arch Gen Psychiatry* 1974; 31:394-7.
Hartmann E, Spinweber C L. Sleep induced by L-Tryptophan: effect of dosages within the normal dietary intake. *J Nerv Ment Dis* 1979; 167:497-9.
Hartmann, E., Greenwald, D., 1984. L-Tryptophan and human sleep: an analysis of 43 studies. In: Schlossberger, H. G., Kochen, W., Linzen, B., Steinhart, H. (Eds.), Progress in L-Tryptophan and Serotonin Research. Walter de Gruyter, Berlin, pp. 297-304.
Hedaya. K. J. Pharmacokinetic factors in the clinical use of L-Tryptophan. Journal of Clinical *Psychopharmacology* 1984; 4:347-348.
Klackenberg G. Incidence of Parasomnias in children in a general population. In: Guilleminault C, editor. *Sleep and its disorders in children*. New York: Raven Press; 1987; 99-113
Levitan R D, Shen J H, Jindal R, Driver H S, Kennedy S H, Shapiro C M. Preliminary randomized double-blind placebo-controlled trial of L-Tryptophan combined with fluoxetine to treat major depressive disorder: antidepressant and hypnotic effects. *J Psychiatry Neurosci.* 2000; 25:337-46.
Petit D, Touchette E, Tremblay R E, Boivin M, Montplaisir J. Dyssomnias and Parasomnias in early childhood. Pediatrics 2007; 119:1016-25.
Riemann D, Feige B, Hornyak M, Koch S, Hohagen F, Voderholzer U. The L-Tryptophan depletion test: In primary insomnia—a pilot study. *Psychiatry Res* 2002; 109: 129-135.
Sainio, E L, Pulkki, K, and Young, S N. L-Tryptophan: Biochemical, nutritional and pharmacological aspects *Amino Acids* 1996; 10:21-47
Schneider-Helmert D, Bodmer M. Definitive recovery from chronic severe insomnia by long term interval therapy with L-Tryptophan. *Sleep Res* 1983; 12:393.
Snyder, S. & Ilams, G. Serotonergic agents in the treatment of isolated sleep paralysis. *American Journal of Psychiatry* 1982; 139:1202-1203.
Sours, J A, Frumkin, P, Indermill R R. SOMNAMBULISM: ITS CLINICAL SIGNIFICANCE AND DYNAMIC MEANING IN LATE ADOLESCENCE AND ADULTHOOD. *Arch Gen Psychiatry.* 1963; 9:400-13.
Young. S N. (1986). The clinical psychopharmacology of L-Tryptophan. In Wurtman, R. J. & Wurtman. J. J. (Eds.). Nutrition and the brain (pp. 49-88). vol. 7, New York: Raven Press.
Wyatt R J, Engelman K, Kupfer D J, Fram D H, Sjoersdma A, Snyder F. Effects of L-Tryptophan (a natural sedative) on human sleep. *Lancet* 1970; 2:842-6.

The invention claimed is:

1. A method of treating a subject with parasomnia associated with arousal from NREM sleep, the method comprising administering to the subject a therapeutically effective amount of L-tryptophan.

2. The method of claim 1, wherein the subject with parasomnia exhibits sleep walking, confusional arousals, night terrors and/or sleep-related eating disorder.

3. The method of claim 1, wherein L-tryptophan is administered orally to the subject.

4. The method of claim 1, wherein L-tryptophan is administered in the evening.

5. The method of claim 1, wherein the L-tryptophan is administered before the subject goes to bed.

6. The method of claim 1, wherein L-tryptophan is administered as a solution.

7. The method of claim 1, wherein L-tryptophan is administered in pill form or as a capsule.

8. The method of claim 1, wherein the subject is a child.

9. The method of claim 8, wherein the child is between 3 and 12 years of age.

10. The method of claim 8, comprising administering to the child a dose of L-tryptophan of about 350 mg to about 2500 mg.

11. The method of claim 1, wherein the subject is an adolescent.

12. The method of claim 11, wherein the adolescent is between 13 and 18 years of age.

13. The method of claim 11, comprising administering to the adolescent a dose of L-tryptophan of about 700 mg to about 3500 mg.

14. The method of claim 1, wherein the subject is an adult.

15. The method of claim 14, wherein the adult is greater than 18 years of age.

16. The method of claim 14, comprising administering to the adult a dose of L-tryptophan of about 700 mg to about 5000 mg.

17. The method of claim 1, wherein the treatment reduces the frequency of parasomnic events in the subject.

18. The method of claim 1, wherein the treatment reduces the severity of parasomnic events in the subject.

19. The method of claim 1, wherein the treatment reduces the frequency of intermittent arousals during slow-wave sleep (SWS) in the subject.

20. The method of claim 1, for treating a subject exhibiting at least two abnormal behaviors or physiological events selected from sleep walking, confusional arousals, sleep-related eating disorder and night terrors.

21. The method of claim 1, for the treatment of sleep walking, confusional arousals or night terrors.

* * * * *